United States Patent [19]

Diamond et al.

[11] Patent Number: 5,426,373

[45] Date of Patent: Jun. 20, 1995

[54] TWO ELECTRODE DEVICE FOR DETERMINING ELECTRICAL PROPERTIES OF A MATERIAL ON A METAL SUBSTRATUM

[75] Inventors: Earl L. Diamond, Annapolis; George I. Loeb, Bethesda; Angela M. Ross, Baltimore, all of Md.

[73] Assignee: The United States of America as represented by the Secretary of the Navy, Washington, D.C.

[21] Appl. No.: 953,387

[22] Filed: Sep. 30, 1992

[51] Int. Cl.$^6$ ............................................. G01R 27/26
[52] U.S. Cl. ........................................ 324/663; 324/457
[58] Field of Search ............... 324/662, 663, 690, 650, 324/452–457, 671; 427/8, 9, 10

[56] References Cited

U.S. PATENT DOCUMENTS

| | | | |
|---|---|---|---|
| 3,671,857 | 6/1972 | Bergmanis et al. | |
| 3,805,150 | 4/1974 | Abbe | 324/662 |
| 4,106,107 | 8/1978 | Goodman | 324/457 |
| 4,806,849 | 2/1989 | Kihira et al. | 427/10 |
| 5,223,796 | 6/1993 | Waldman et al. | 324/690 |
| 5,309,110 | 5/1994 | O'Neill et al. | 324/663 |

FOREIGN PATENT DOCUMENTS

| | | | |
|---|---|---|---|
| 0302727 | 2/1979 | European Pat. Off. | 324/663 |
| 2003613 | 3/1979 | United Kingdom | 324/650 |
| 0748286 | 7/1980 | U.S.S.R. | 324/650 |
| 1543331 | 2/1990 | U.S.S.R. | 324/663 |

OTHER PUBLICATIONS

Journal of Physics vol. 9. Jan. 26, 1976 Baker et al. A Simple Technique for Measuring Nonlinear AC Properties of Materials at Frequencies Flow 1Hz.

*Primary Examiner*—Maura K. Regan
*Attorney, Agent, or Firm*—Charles D. Miller

[57] ABSTRACT

A device for determining electrical properties of a dielectric material on a metal substratum is provided. First and second electrodes are suspended in a spaced apart relationship above the dielectric material thereby forming first and second air gaps, respectively, between the electrodes and the dielectric material. A resulting circuit path is formed that includes the first and second electrodes, the first and second air gaps, the dielectric material and the metal substratum. Changes in the measured complex impedance of the circuit path are indicative of the electrical properties of the dielectric material.

16 Claims, 1 Drawing Sheet ic
TWO ELECTRODE DEVICE FOR DETERMINING ELECTRICAL PROPERTIES OF A MATERIAL ON A METAL SUBSTRATUM The invention described herein may be manufactured and used by or for the Government of the United States of America for governmental purposes without payment of any royalties thereon or therefor.

1. Field of the Invention

The invention relates generally to the determination of electrical properties of a material, and more particularly to a device for determining electrical properties of a material that is coated or painted onto a metal substratum. The change in electrical properties over time is used to indicate the condition of the coatings or paints.

2. Background of the Invention

It has been known for some time that a protective coating or paint (as it will be referred to hereinafter for sake of simplicity) deteriorates as a function of time with respect to, for example, moisture protection. Thus, the substratum to which the paint has been applied may be subject to moisture damage even though the paint appears to be sound. Accordingly, methods have been developed to analyze the structural integrity of a paint. In one method, it has been shown that examination of dielectric properties of a paint over time can be used to determine the condition of the paint. More specifically, a paint's dielectric constant can be multiplied by a dissipation factor to generate a loss index which, when knowing the paint's initial loss index, indicates the condition of the paint. The change in loss index over relatively short periods of time (e.g., one week or one month) during aging is indicative of the paint's long term aging characteristics. The loss index of higher quality paints changes less than one order of magnitude during aging while the loss index of poorer quality paints may change by 9 or 10 orders of magnitude within one month.

The process of examining dielectric properties of a paint (or any dielectric material) is somewhat facilitated when the substratum to which the paint is applied is metal. However, prior art determination of the above mentioned electrical properties of a paint required direct contact with the metal substratum. In certain instances (e.g., checking paint on a ship's hull), such contact either required the use of excessively long electrical leads or required that the paint be scratched off to expose the metal substratum.

SUMMARY OF THE INVENTION

Accordingly, it is an object of the present invention to provide a device that can be used to determine the condition of a paint applied to a metal substratum such that the device need not contact the substratum.

Another object of the present invention is to provide a device that can determine electrical properties of any dielectric material applied on a metal substratum such that the device need not contact the substratum.

Yet another object of the present invention is to provide a device that can determine electrical properties of a dielectric material applied on a metal substratum that is simple and easy to operate.

Other objects and advantages of the present invention will become more obvious hereinafter in the specification and drawings.

In accordance with the present invention, a device for determining electrical properties of a dielectric material on a metal substratum is provided. First and second electrodes are suspended in a spaced apart relationship above the dielectric material. A first air gap is formed between the first electrode and the dielectric material while a second air gap is formed between the second electrode and the dielectric material. Electrically connected to the first and second electrodes is a means for measuring a complex impedance of a circuit path that includes the first and second electrodes, the first and second air gaps, the dielectric material and the metal substratum. Changes in the measured complex impedance are indicative of the electrical properties of the dielectric material.

DETAILED DESCRIPTION OF THE INVENTION

Figure 1:
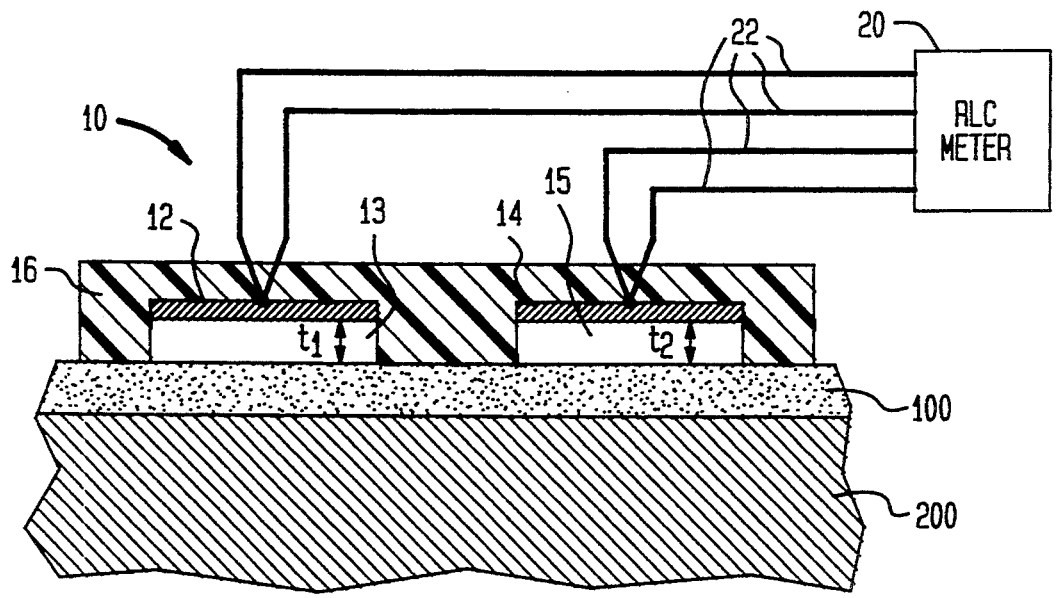
FIG. 1 is a side, cross-sectional view of the two electrode device as it is used in accordance with the present invention.

Referring now to the drawings, and more particularly to FIG. 1, a side, cross-sectional view is shown of the two electrode device 10 as it would be used to determine electrical properties of a material 100 applied to a metal substratum 200. Material 100 might be a paint, protective coating or any other dielectric material whose thickness is known.

Device 10 consists of two electrodes 12 and 14 held in suspension above material 100 by a housing 16. Electrodes 12 and 14 are chosen to be identically sized thin-film electrodes ranging from 0.02–0.05 inches thick in order to minimize edge effects. However, it is to be understood that electrodes 12 and 14 may be of any thickness that is practical to fabricate. Electrodes 12 and 14 may be fabricated from a metal or other conductive solid, and may further be flexible. By way of example, it will further be assumed that electrodes 12 and 14 are of circular cross-section and have a diameter of approximately one inch. However, as will be explained further hereinbelow, the cross-sectional shape and size of electrodes 12 and 14 is not critical to the present invention. Housing 16 may be constructed from any rigid or flexible dielectric material that can support electrodes 12 and 14 in suspension above material 100. By way of example, housing 16 may be constructed of a fiberglass laminate. Housing 16 may alternatively be spaced above material 100 by means of a separate spacer.

By virtue of suspending electrodes 12 and 14 above material 100 as shown, air gaps 13 and 15 are respectively formed between material 100 and electrodes 12 and 14. Air gaps 13 and 15 have known constant thickness $t_1$ and $t_2$. Air gaps 13 and 15 may be configured such that $t_1 = t_2$, as is the case in the preferred embodiment. The thicknesses $t_1$ and $t_2$ are preferably chosen to be less than 20% of the thickness of material 100 where possible. Widths greater than 20% may reduce the accuracy of the measurement. Such sizing is in accordance with specifications set forth in the American Society for Testing and Materials in the standard test method ASTM-D150, the teachings of which awe hereby incorporated by reference.

Electrodes 12 and 14 are connected to an RLC meter 20 in order to measure complex impedance as described further hereinbelow. In the preferred embodiment, RLC meter 20 is connected to electrodes 12 and 14 by four leads 22 and is configured to measure complex impedance in the four terminal Kelvin mode as is well known in the art. See "Electrical Measurements", by Forest K. Harris, John Wiley and Sons, Inc., 1952, page 283. The four terminal connection to the electrodes is used to eliminate lead errors from the measurements. In this way, the effective measurement point is brought to the actual electrodes.

Figure 2:
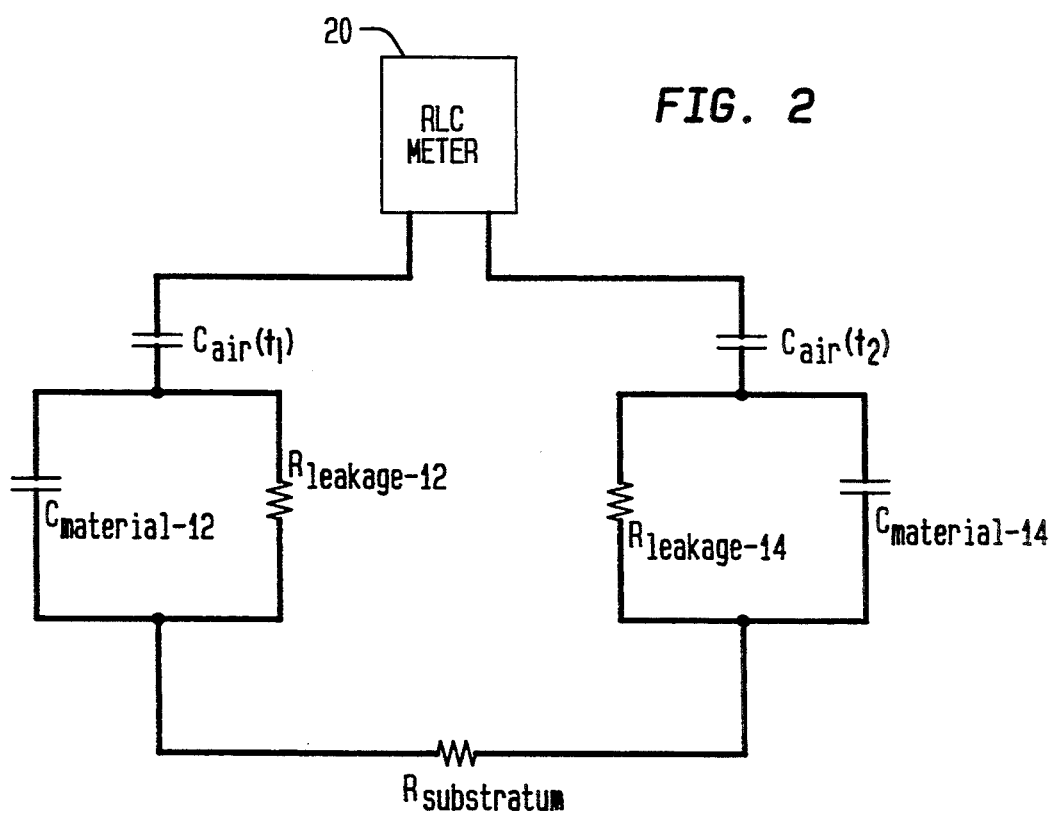
FIG. 2 is an equivalent circuit for the two electrode device as shown in FIG. 1.

In order to understand the operating principles of the present invention, simultaneous reference will now be made to FIG. 2 which depicts an equivalent circuit for the two electrode device shown in FIG. 1. Common reference numerals will be used When making reference to the circuit elements in FIG. 2 as they relate to the physical elements in FIG. 1. In particular, when the two electrode device 10 is placed on the surface of material 100, a series circuit is formed that includes RLC meter 20, electrodes 12 and 14, air gaps 13 and 15, material 100 and metal substratum 200. Electrode 12 and substratum 200 act as plates of a first capacitor while electrode 14 and substratum 200 act as plates of a second capacitor. As shown, a first complex impedance exists between electrode 12 and substratum 200 and is designated as follows:

$C_{air}(t_1)$ is the capacitance across air gap 13 as a function of thickness $t_1$, $C_{material-12}$ is the capacitance across material 100 beneath the area of electrode 12, and $R_{leakage-12}$ is the resistance due to the porosity of material 100 beneath the area of electrode 12. This is a function of the dissipation factor of material 100 as is known in the art.

In a similar fashion, a second complex impedance exists between electrode 14 and substratum 200 and is designated as follows:

$C_{air}(t_2)$ is the capacitance across air gap 15 as a function of thickness $t_2$, $C_{material-14}$ is the capacitance across material 100 beneath the area of electrode 14, and $R_{leakage-14}$ is the resistance due to the porosity of material 100 beneath the area of electrode 14. For purposes of the preferred embodiment, it will be assumed that material 100 is of uniform thickness and porosity underneath electrodes 12 and 14. Practically speaking, this will generally be true in any localized area of material 100.

A resistance $R_{substratum}$ is shown in the series equivalent circuit. Since the substratum is metal, series resistance $R_{substratum}$ is negligible (i.e., less than 52 micro-ohms) in the complex impedance measurement. Furthermore, since the four capacitances share a common electrode plate (i.e., metal substratum 200), the four capacitances are in series with one another for purposes of a complex impedance measurement. RLC meter 20 completes the circuit and is used to measure the complex impedance of the circuit.

Since the capacitances $C_{air}(t_1)$ and $C_{air}(t_2)$ are known, the capacitances $C_{material-12}$ and $C_{material-14}$ may be used to determine the dielectric constant of material 100 as taught in ASTM-D150. The dissipation factor for material 100 may be determined from $R_{leakage-12}$ and $R_{leakage-14}$ as taught in ASTM-D150. Once the dielectric constant and dissipation factor of material 100 are known, the loss index of material 100 can easily be determined as is known in the art. Thus, when measurements are performed over time, changes in measurements are due only to changes in the properties of material 100.

The air gaps 13 and 15 are included in the design since it would be very difficult to place electrodes 12 and 14 in flush communication with material 100 as any attempt to do so would always introduce some air gaps due to surface irregularities on material 100. Accordingly, air gaps 13 and 15 provide a known standard (i.e., known thickness and dielectric constant) such that any change in capacitance measured by RLC meter 20 is in proportion only to the dielectric constant associated with material 100.

The advantages of the present invention are numerous. The two electrode device provides for the measurement of electrical properties of a paint, coating or any dielectric material on a metal substratum without requiring direct electrical contact with the metal substratum. This eliminates any need to damage the coating near the position of measurement in order to make contact with the metal substratum. This also eliminates the need for long electrical lends to make contact with the metal substratum at some distant position.

Although the invention has been described relative to a specific embodiment thereof, there are numerous variations and modifications that will be readily apparent to those skilled in the art in the light of the above teachings. For example, the entire two electrode device may be rigid (for flat surfaces) or flexible (for curved surfaces). The two electrodes may be housed in a single structure as in the preferred embodiment. Alternatively, two separate electrode structures may be used for measurement of very irregularly shaped surfaces. Finally, while the preferred embodiment utilizes air gaps of known thickness, the air gaps could be filled with a gel-like dielectric material (having a known dielectric constant) that could conform to the surface of the material to be measured. This would provide the added benefit of protecting the electrodes from damage. It is therefore to be understood that, within the scope of the appended claims, the invention may be practiced other than as specifically described.

What is claimed is:

1. A device for determining electrical properties of a dielectric material on a metal substratum, comprising:
    a first electrode;
    a second electrode;
    means for suspending said first and second electrodes in a spaced apart relationship above and on the same side of the dielectric material wherein a first air gap is formed between said first electrode and the dielectric material and wherein a second air gap is formed between said second electrode and the dielectric material; and
    means, electrically connected to said first and second electrodes, for measuring a complex impedance of a circuit path that includes said first and second electrodes, said first and second air gaps, the dielectric material and the metal substratum, wherein changes in the measured complex impedance are indicative of the electrical properties of the dielectric material and no external electrical contact with said metal substratum is made when the complex impedance is being measured.

2. A device as in claim 1 wherein said finest and second electrodes are thin-film electrodes whose thickness ranges between 0.02 and 0.05 inches.

3. A device as in claim 2 wherein said first and second electrodes are circular in cross-section.

4. A device as in claim 1 wherein said suspending means is a fiberglass material.

5. A device as in claim 1 wherein each of said first and second air gaps are of constant thickness.

6. A device as in claim 1 wherein each of said first and second air gaps are of equal and constant thickness.

7. A device as in claim 5 wherein the thickness of each of said first and second air gaps is selected to be less than 20% of the thickness of the dielectric material above which the corresponding first and second electrodes have been suspended.

8. A device as in claim 1 wherein said finest and second air gaps are filled with a material possessing a known dielectric constant.

9. A device as in claim 1 wherein said measuring means is an RLC meter electrically connected to said first and second electrodes according to a four terminal Kelvin mode.

10. A device for determining electrical properties of a dielectric material on a metal substratum, comprising:
   means to be located on a first side of said dielectric material for forming a first capacitor, wherein a portion of said dielectric material forms said first capacitor's dielectric and wherein a portion of the metal substratum forms one of said first capacitor's electrodes;
   means, to be located on said first side of said dielectric material for forming a second capacitor in a spaced apart relationship from said first capacitor, wherein a portion of the said dielectric material forms said second capacitor's dielectric, and wherein a portion of the metal substratum forms one of said second capacitor's electrodes, whereby the remaining metal substratum provides electrical connection between each of said first and second capacitor forming means and connects said first and second capacitors in series; and
   means for measuring the complex impedance of the said circuit path, wherein changes in the measured complex impedance are indicative of the electrical properties of the dielectric material.

11. A device as in claim 10 wherein said first capacitor forming means comprises a first electrode spaced above the dielectric material by a first constant thickness air gap, and wherein said second capacitor forming means comprises a second electrode spaced above the dielectric material by a second constant thickness air gap.

12. A device as in claim 11 wherein said first and second constant width air gaps each form less than 20% of corresponding said first and second capacitor's dielectric.

13. A device as in claim 11 wherein said first and second constant thickness air gaps are filled with a material possessing a known dielectric constant.

14. A device as in claim 11 wherein said first and second constant thickness air gaps are equal.

15. A device as in claim 10 wherein said measuring means is an RLC meter electrically connected to said first and second capacitor forming means according to a four terminal Kelvin mode.

16. A device for determining the electrical properties of a dielectric material which is coated onto a metal substrata comprising:
   a complex impedance measuring means;
   electrode means for placement over the said coated material so that at least two capacitors are formed from the combination of said electrode means along with the said material and the said metal substrate,
   said two capacitors being electrically connected in series and to said impedance measuring means, whereby the dielectric properties of said material can be determined.

* * * * *